United States Patent [19]

Wang et al.

[11] Patent Number: 4,962,673
[45] Date of Patent: Oct. 16, 1990

[54] PRESSURE REDUCTION DEVICE FOR PARTICLE SAMPLING FROM COMPRESSED GASES

[75] Inventors: Hwa-Chi Wang, Downers Grove; Donnel Montgomery, Chicago; Horng-Yuan Wen, Brookfield; Gerhard Kasper, Downers Grove, all of Ill.

[73] Assignee: American Air Liquide, Countryside, Ill.

[21] Appl. No.: 320,504

[22] Filed: Mar. 8, 1989

[51] Int. Cl.$^5$ .............................................. G01N 1/22
[52] U.S. Cl. ................................................. 73/864.73
[58] Field of Search ........... 73/864.73, 864.74, 863.21, 73/863.81, 863.41

[56] References Cited

U.S. PATENT DOCUMENTS

| | | | |
|---|---|---|---|
| 3,289,481 | 12/1966 | Barnes | 73/864.73 X |
| 3,522,734 | 8/1970 | Lurby | 73/864.73 X |
| 4,032,395 | 6/1977 | Burnette | 73/864.73 X |
| 4,586,390 | 5/1986 | Helke | 73/864.73 |

FOREIGN PATENT DOCUMENTS 1084649  4/1984  U.S.S.R. ........................... 73/864.73

Primary Examiner—Tom Noland
Attorney, Agent, or Firm—Oblon, Spivak, McClelland, Maier & Neustadt

[57] ABSTRACT

Disclosed is a device for particle sampling from compressed gases. The device allows for anayzing particles from compressed gases of a pressure ranging from 20 psi to 3000 psi. In the device, the formula $D_s = D_t \sqrt{(Q_s/Q_t)}$ is applicable wherein $D_s$ and $D_t$ are the probe diameter and the chamber diameter, respectively, $Q_s$ is the sampling flow rate required by monitoring instruments, and $Q_t$ is the total flow rate determined by the orifice diameter and pressure whereby the sampling velocity substantially matches the local flow velocity at the probe. In addition, a distance between the orifice and the probe is greater than L wherein $L = D_c/(2 \tan \alpha)$ where $D_c$ is the chamber diameter and $\alpha$ is the half angle of jet expansion.

9 Claims, 8 Drawing Sheets

TO HIGH
PRESSURE
GAS SOURCE 10

|  | 1" – PR PARTICLES/SCF | 3" – PR PARTICLES/SCF |
|---|---|---|
| BACKGROUND | 0 | 0 |
| TEST 1 | 11779 | 11270 |
| TEST 2 | 12232 | 9476 |
| TEST 3 | 11873 | 10326 |
| TEST 4 | 11703 | 13497 |
| TEST 5 | 13553 | 13837 |
| TEST 6 | 13158 | 13308 |
| AVERAGE | 12383 | 11952 |
| STD. DEV. | 716 | 1684 |
| COV. | 5.8% | 14.1% |

*FIG. 8*

| TIME (hr) | NORMALLY CLEANED ORIFICE | | TWO SPECIALLY CLEANED ORIFICES | | | |
|---|---|---|---|---|---|---|
| | LPC (ft⁻³) | CNC (ft⁻³) | LPC (ft⁻³) | CNC (ft⁻³) | LPC (ft⁻³) | CNC (ft⁻³) |
| 1 | 0 | 8 | 4 | 6 | 0 | 2 |
| 2 | 2 | 6 | 8 | 2 | 3 | 0 |
| 3 | 4 | 5 | 2 | 3 | 1 | 0 |
| 4 | 1 | 2 | 0 | 3 | 0 | 0 |
| 5 | 10 | 3 | 0 | 2 | 0 | 0 |
| 6 | 6 | 0 | 2 | 0 | 0 | 0 |
| 7 | 4 | 10 | 1 | 0 | 0 | 0 |
| 8 | 110 | 6 | 1 | 0 | 0 | 0 |
| 9 | 55 | 6 | 1 | 2 | 0 | 0 |
| 10 | 97 | 21 | 0 | 0 | 0 | 0 |
| 11 | 116 | 14 | 0 | 0 | 0 | 0 |
| 12 | 139 | 24 | 0 | 0 | 0 | 0 |
| 13 | | 13 | | | | 0 |
| 14 | | 195 | | | | 0 |
| 15 | | 32 | | | | 0 |
| 16 | | 78 | | | | 0 |
| 17 | | 8 | | | | 0 |
| 18 | | 96 | | | | 0 |
| 19 | | 88 | | | | 0 |
| 20 | | 5 | | | | 0 |
| 21 | | 178 | | | | 0 |
| 22 | | 133 | | | | 0 |
| 23 | | 90 | | | | 0 |
| 24 | | 107 | | | | 0 |

FIG. 9

PRESSURE REDUCTION DEVICE FOR PARTICLE SAMPLING FROM COMPRESSED GASES

BACKGROUND OF THE INVENTION

1. Field of the Invention:

An orifice-type pressure reduction device compatible with particle sampling from compressed, high-purity gases is described.

2. Discussion of the Background:

Pressure reduction is a necessary step in sampling particles from compressed gases because most particle counters operate at or near atmospheric pressure. The criteria for a good pressure reducing device are that the particle loss is negligible and no artifact particles are generated.

It has been discovered from past experience that pressure regulators, needle valves and other commonly used flow control devices cannot be used for particle sampling because particles are lost in an uncontrolled fashion.

Pressure reduction by expanding gases through a capillary type pressure reducer tube for sampling from pressurized gas line has been used, for example in the high pressure diffuser shown in FIG. 1. FIG. 1 discloses a diffuser 1, needle assembly 2, end cap 3, jet guard 4, diffuser mount 5 and case member 6. An inlet jet 7, adapter fitting 8, hex cell 9 and high pressure gas source 10 are also utilized. This method and device has a severe drawback with respect to cleanability which thus prevents its application in high purity gases. Previous data ("Particles in Ultrasonic Process Gases", G. Kasper and Y. Wen Handbook of Contamination Control in Microelectronics Industry, Jan., 1988) have shown that the device itself is an indefinite source of particles.

Expanding gases through a thin orifice disc was recognized as the most suitable method of reducing pressure for particle analysis (Wen and Kasper, 1988, Journal of Aerosol Research, Japan; 1988 SEMI International Standards). The fluid dynamics for flow passing through an orifice has been well documented.

SUMMARY OF THE INVENTION

The object of the present invention is to optimally design an orifice-type pressure reduction device for analyzing particles from compressed gases of a pressure ranging from 20 psi to 3000 psi and to provide a corresponding method.

A further object of the present invention is to provide an orifice-type pressure reduction device which is capable of sampling particles from compressed gases with minimum particle loss and no artifact particle generation.

A further object of the invention is to provide a pressure reduction device with exchangeable sample probes to achieve isokinetic sampling for a wide range of applications.

An additional object of the invention is to provide a pressure reduction device with proper arrangement between the orifice and sampling probe to minimize particle sampling error due to non-uniform concentration profile and wall loss in the expansion chamber.

A further object of the invention is to provide a pressure reduction device so as to utilize an orifice holder that is compatible with high-purity gas, is bakable, and is easily adaptable to various gases up to 3000 psi.

A yet additional object of the invention is to provide a pressure reduction device equipped with an electropolished, cleaned orifice disc, which generates practically no artifact particles during the process of pressure reduction.

BRIEF DESCRIPTION OF THE DRAWING

Various other objects, features and attendant advantages of the present invention will be more fully appreciated as the same becomes better understood from the following detailed description when considered in connection with the accompanying drawings in which like references characters designate like or corresponding parts throughout the several views and wherein:

FIGS. 7 and 9 relate to cleaning of the orifice; and

FIG. 8 relates to the dimensions of the expansion chamber.

DESCRIPTION OF THE PREFERRED EMBODIMENT

Figure 1:
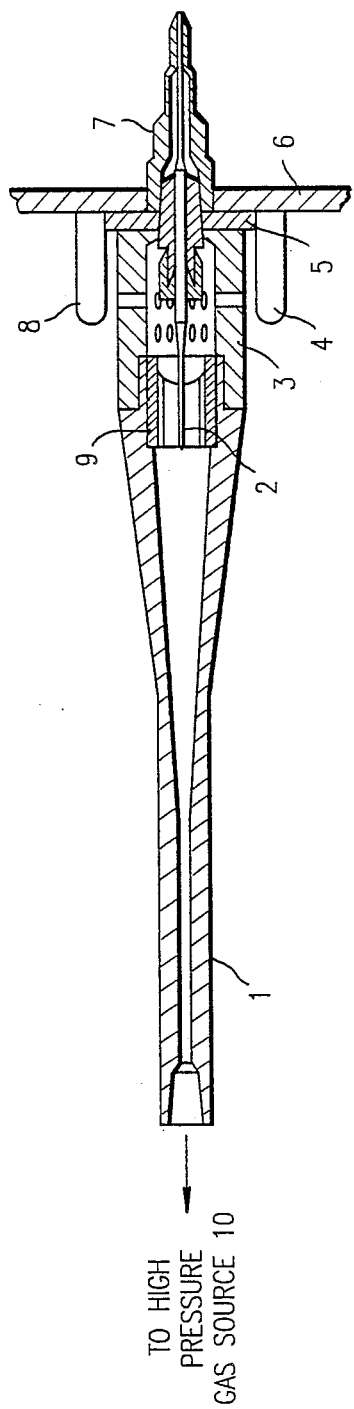
FIG. 1 discloses a conventional capillary type pressure reducer for sampling from pressurized gas lines.
Figure 2:
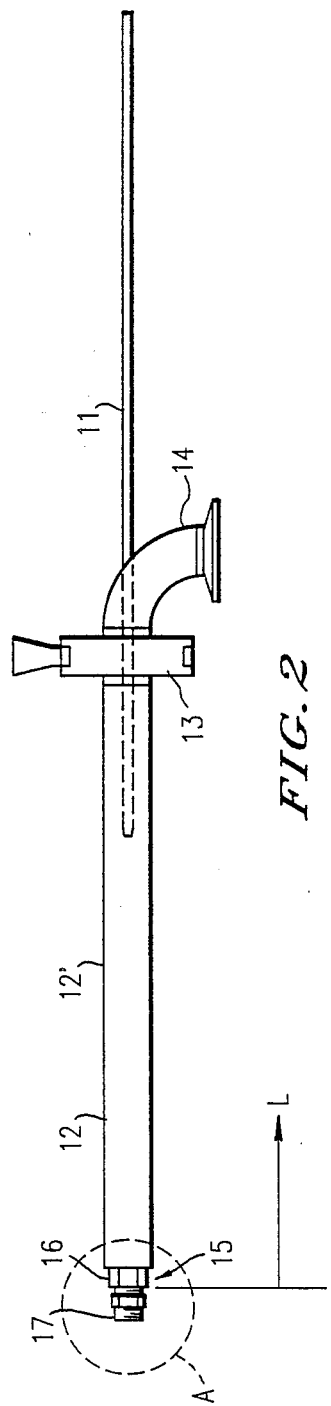
FIG. 2 shows an orifice-type pressure reducing device in accordance with the present invention.

FIG. 2 illustrates the orifice-type pressure reducing device in a preferred embodiment in accordance with the present invention. Such is utilized for sampling particles from bulk gases where the dimensions of the device can be varied, according to the criteria detailed hereinbelow to meet different applications. This device and its corresponding method of operation offers flexible flow rates, has negligible particle loss, does not generate artifact particles and provides representative particle samples to the measuring instruments.

Figure 2A:
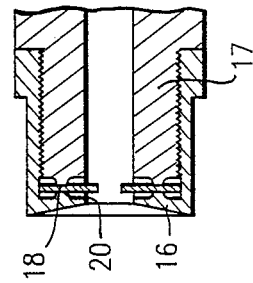
FIG. 2A shows the details of the structure indicated by circle A in FIG. 2.

As shown in FIG. 2, a straight sampling probe 11 is utilized which extends within a tubular member 12' defining an expansion chamber 12. Probe 11 is straight to prevent particle loss and its length is variable, depending on sampling conditions. A securing member in the form of a flange, gasket and clamp assembly 13 is shown which connects an elbow 14 to the tube 12' forming expansion chamber 12. Probe 11 is slidable within an opening (not shown) in elbow 14. A gasket assembly 15 is formed at an upstream end portion of the expansion chamber 12 and includes an orifice disc holder 16, a double male fitting 17 fitted within orifice disc holder 16 and an orifice disc 18 secured between disc holder 16 and fitting 17, as more clearly illustrated in FIG. 2A and is upstream of an opening 20 in disc holder 16. It is to be recognized, however, that tubular member 12' and elbow 14 could be a single member.

To obtain a desired flexible flow rate in gases, the orifice diameter and/or pressure can be changed according to the formula:

$$Q = C\, D^2\, P/\sqrt{T}$$

wherein Q is the flow rate in standard liters per minute, D is the hole diameter in mm, P is upstream gas pressure in psia, and T is upstream gas temperature in degrees K.

Figure 3:
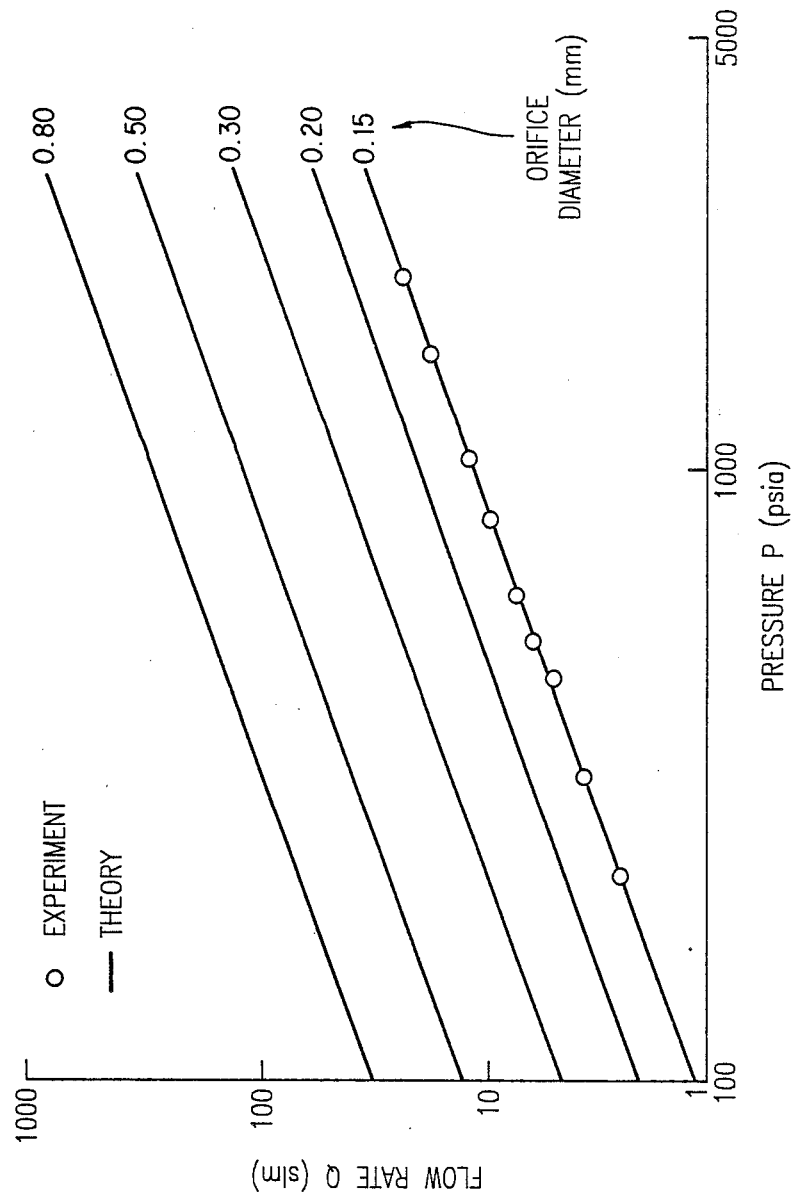
FIGS. 3 and 4 show the flow rates as a function of pressure for various orifice diameters.
Figure 4:
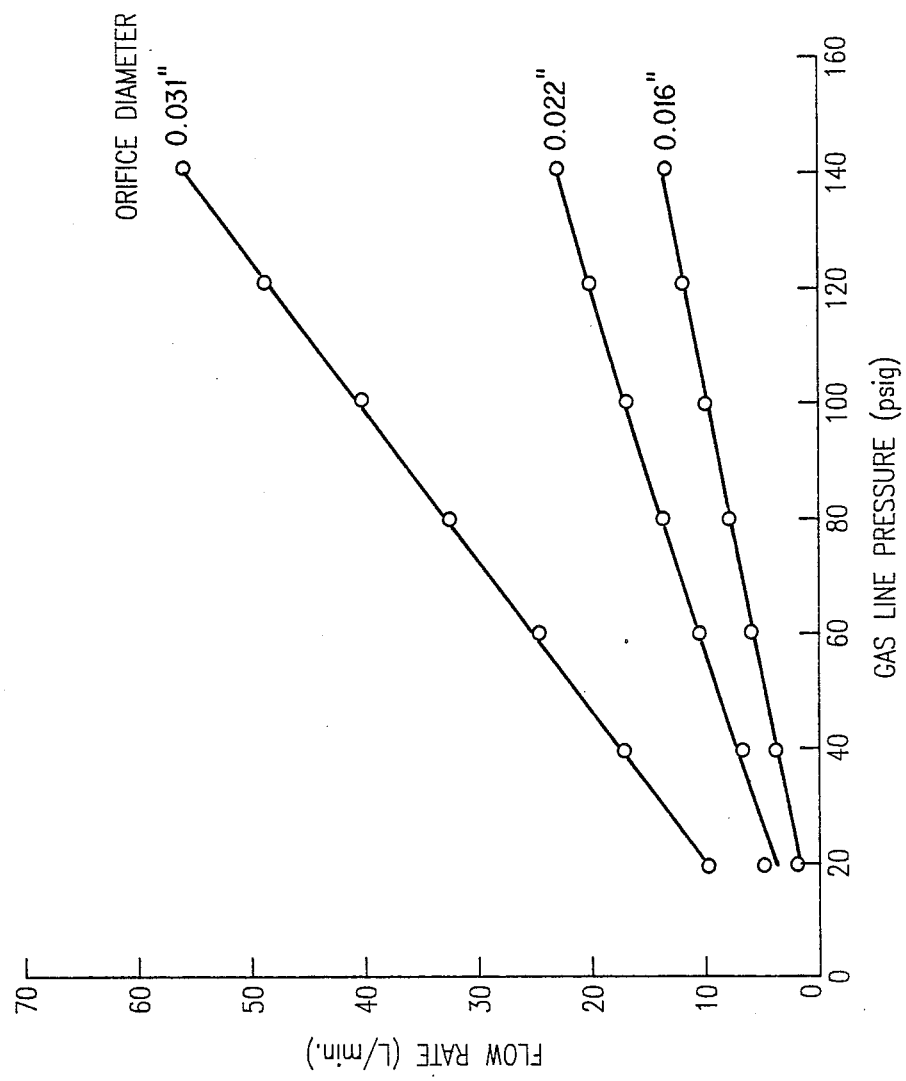

The constant C=8.34 is for nitrogen and varies slightly for gases with different ratios of specific heat. Experimental data as well as theoretical predictions for a range of orifice diameters and pressure are given in FIGS. 3 and 4. This flow rate should exceed the intake flow rate of the employed particle analyzing instruments.

Figure 5:
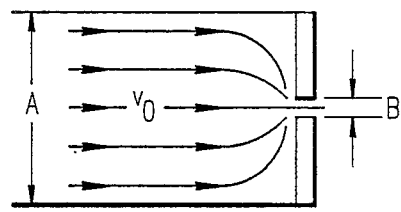
FIG. 5 shows the convergence of flow near the orifice, which causes impaction losses of particles upstream of the orifice plate.
Figure 6:
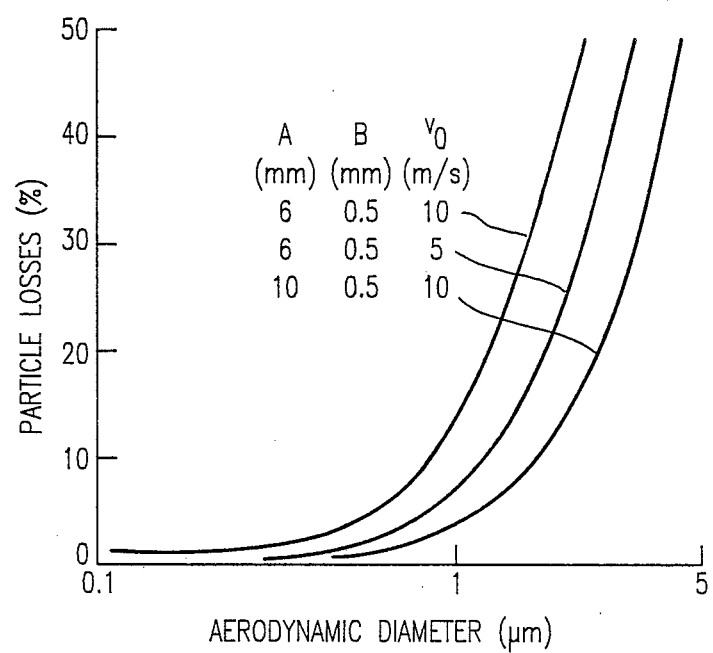
FIG. 6 shows impaction losses of particles on the orifice plate of FIG. 5.

Particle loss in this device may occur upstream and downstream of the orifice. The upstream particle loss results primarily from impaction near the orifice where flow converges sharply. According to the model published by Wen and Kasper (1988, Journal of Aerosol Research, Japan), particle loss is not significant for particles smaller than 2 μm for ordinary applications as shown in FIGS. 5 and 6. The loss can be further reduced by increasing the diameter of the upstream tubing.

Figure 7:
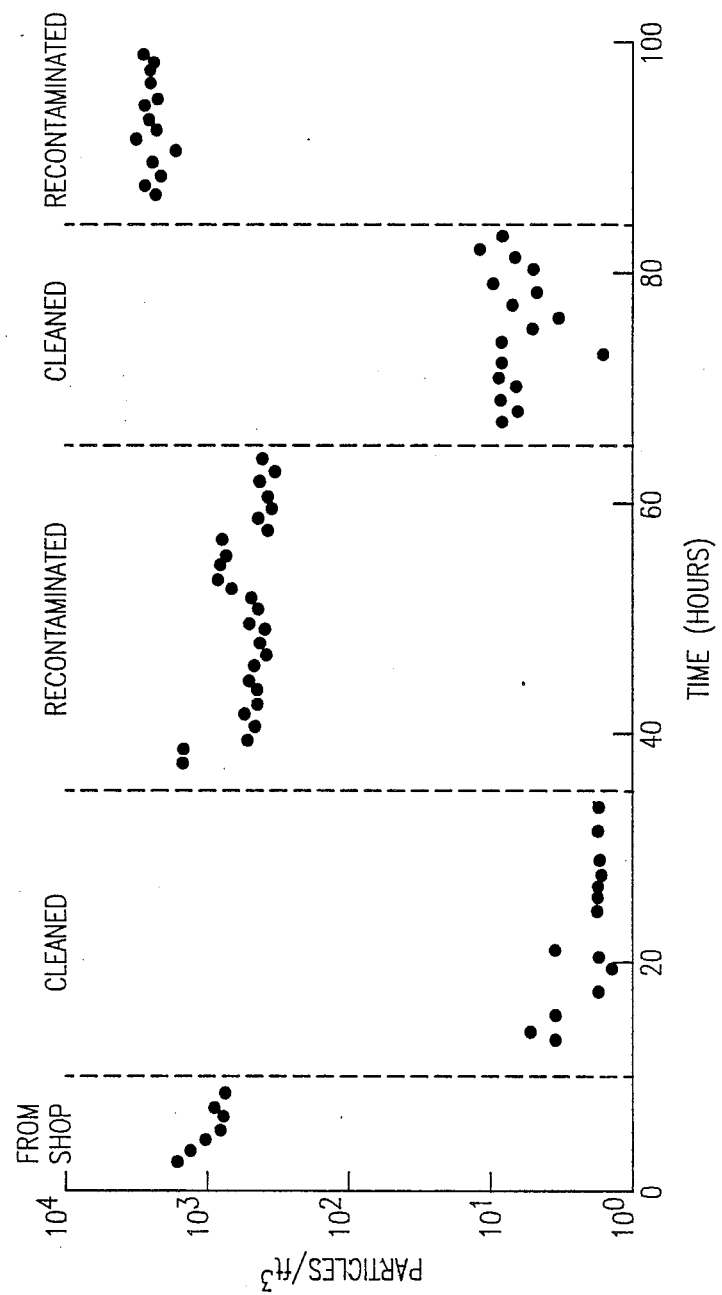

The downstream particle loss occurs when the expanding jet hits the wall of the downstream tubing. This loss may be important if the total flow rate is comparable with the intake flow rate of the monitoring instrument. In the design of devices for taking samples from the center portion of the well-mixed flow, the downstream particle loss is not important. In any case, a large diameter for the downstream tubing helps by preventing particle loss. Comparison of the results from 3-inch and 1-inch diameters for the tubing of the pressure reducer, shown in the table of FIG. 7, indicates no observable difference, suggesting that a 1-inch system is large enough to serve the purpose.

To prevent artifact particles under a wide range of applications, three criteria must be followed: proper material selection, adequate orifice preparation, and proper design of the orifice holder. Only clean parts, for example electro-polished tubings or other alternatives with comparable surface finish, should be used.

The orifice preparation is the most critical step to achieve "zero" particle generation. An orifice diameter in the range of 0.006" to 0.100", depending upon the flow rate requirement, can be obtained by mechanical drilling. For a smaller orifice (<0.006"), a laser drilling technique can be applied. Subsequent cleaning procedures determine the performance of the orifice.

FIG. 8 shows the artifact particles generated by the orifice immediately after drilling and with subsequent cleaning. The necessity of cleaning after drilling and contamination is obvious. It also indicates that cleaning can reduce artifact particle concentration by 3 orders of magnitude. A variety of cleaning procedures can serve the purpose, such as jet wash, ultrasonication, acid etching, etc. However, proper precaution and the purity of the employed solvent are critical.

FIG. 9 shows the artifact particles generated by orifices with different degrees of cleanliness. The condensation nucleus counter (CNC) registers all particles larger than 0.01 μm and the laser particle counter (LPC) registers particles greater than 0.1 μm. A thoroughly cleaned orifice (Orifice 3 in FIG. 9) can achieve less than 0.1 artifact particles per cubic foot on the CNC level over 24 hours.

The orifice holder 16 must be leak-proof. To be compatible with high purity gases, use of electro-polished fittings (VCR) or equivalent alternatives is necessary. The holder 16 is modified from a VCR cap as shown in FIG. 2. The orifice disc 18 is sandwiched between a VCR male fitting, used for fitting, 17 and the holder 16. The seal relies on the smooth surfaces of the fittings and the orifice disc 18. Since no plastic material is used, this unit can be baked and used for all gases compatible with stainless steel.

To obtain a representative particle sample, the dimensioning and positioning of the sampling probe 11 (for example, ¼" tubing in FIG. 2) are critical. Also, the arrangement of the elbow 14 downstream of the expansion chamber 12 enables a straight sampling probe 11 to be aligned with the flow direction.

The dimension of the sampling probe 11 is governed by the criterion of isokinetic sampling, which requires matching of the sampling velocity to the local flow velocity at the probe 11. Therefore, $$D_s = D_t \sqrt{(Q_s/Q_t)}$$

where $D_s$ and $D_t$ are probe diameter and chamber diameter, respectively, $Q_s$ is the sampling flow rate required by the monitoring instruments, and $Q_t$ is the total flow rate determined by the orifice diameter and pressure.

The position of the sampling probe 11 is determined by the flow pattern in the chamber 12. To avoid the flow disturbance by the downstream elbow 14, the probe 11 needs to be placed a distance at least 5 diameters of the expansion chamber 12 upstream of the elbow 14. The distance between the orifice 18 and the probe 11 should be greater than L as given by the formula:

$$L = D_c/(2 \tan \alpha)$$

where $D_c$ is the chamber diameter and $\alpha$ is the half angle of jet expansion. For an orifice operating under a critical flow condition, $\alpha$ usually is 7±2 degrees. The particle concentration becomes uniform across the cross section of the chamber 12 at a distance L downstream of the orifice 18. Accordingly, the sampling probe should be placed at the center of the chamber and at a distance greater than L from the orifice 18.

The embodiment shown in FIG. 2 was designed, according to the criteria outlined above, for the following conditions:
1. Orifice diameter=0.030 inch
2. Total flow rate~1.1 scf/min at 100 psi
3. Sampling flow rate~0.06 scf/min Additional advantages of this design include small physical size, an exchangeable sampling probe for accommodating a different sampling flow rates, and direct connection to the exhaust system.

Obviously, numerous modifications and variations of the present invention are possible in light of the above teachings. It is therefore to be understood that within the scope of the appended claims, the invention may be practiced otherwise than as specifically described herein.

What is new and desired to be secured by letters patent of the United States is:

1. An orifice-type pressure reducing device for analyzing particles from compressed gases, which comprises:
   an expansion chamber;
   a clean orifice disc positioned at an upstream end portion of said expansion chamber; and
   a sample probe positioned in said expansion chamber.
2. The device as set forth in claim 1, wherein $$D_s = D_t \sqrt{(Q_s/Q_t)}$$

wherein $D_s$ and $D_t$ are the probe diameter and the chamber diameter, respectively, $Q_s$ is the sampling flow rate required by monitoring instruments, and $Q_t$ is the total flow rate determined by the orifice diameter and pressure whereby the sampling velocity substantially matches the local flow velocity at the probe.

3. The device according to claim 1, wherein a distance between the orifice and the probe is greater than L wherein $$L = D_c/(2 \tan \alpha)$$

where $D_c$ is the chamber diameter and $\alpha$ is the half angle of jet expansion.

4. The device according to claim 3, wherein the half angle of jet expansion is $7° \pm 2°$.

5. The device according to claim 1, which comprises electro-polished fitting means for securing said orifice plate in position wherein said orifice plate has smooth metal surfaces so as to be compatible with high purity gases and so as to be bakable.

6. The device according to claim 1, wherein said sampling probe comprises a straight probe.

7. The device according to claim 1, which comprises an elbow member connected to said expansion chamber downstream of said expansion chamber.

8. The device according to claim 7, wherein a tip portion of said sampling probe is positioned a distance upstream of said elbow member at least five times the diameter of said expansion chamber.

9. The device according to claim 7, which comprises means for connecting said expansion chamber to said elbow member.

* * * * *